US012611425B2

(12) United States Patent
Rongved et al.

(10) Patent No.: US 12,611,425 B2
(45) Date of Patent: Apr. 28, 2026

(54) COMPOSITIONS AND METHODS FOR TREATMENT AND PREVENTION OF PATHOGENS

(71) Applicant: WIAB WATER INNOVATION AB, Malmo (SE)

(72) Inventors: Pål Rongved, Oslo (NO); Aina Kristin Pham, Fornebu (NO)

(73) Assignee: WIAB WATER INNOVATION AB, Malmo (SE)

( * ) Notice: Subject to any disclaimer, the term of this patent is extended or adjusted under 35 U.S.C. 154(b) by 287 days.

(21) Appl. No.: 18/449,222

(22) Filed: Aug. 14, 2023

(65) Prior Publication Data

US 2024/0122971 A1     Apr. 18, 2024

Related U.S. Application Data

(60) Provisional application No. 63/414,719, filed on Oct. 10, 2022.

(51) Int. Cl.

| | |
|---|---|
| *A61K 33/20* | (2006.01) |
| *A01N 25/34* | (2006.01) |
| *A01N 37/04* | (2006.01) |
| *A01P 1/00* | (2006.01) |
| *A61K 9/00* | (2006.01) |
| *A61K 9/20* | (2006.01) |
| *A61K 9/46* | (2006.01) |
| *A61P 31/04* | (2006.01) |

(52) U.S. Cl.
CPC .............. *A61K 33/20* (2013.01); *A01N 25/34* (2013.01); *A01N 37/04* (2013.01); *A01P 1/00* (2021.08); *A61K 9/0007* (2013.01); *A61K 9/0078* (2013.01); *A61K 9/2009* (2013.01); *A61K 9/2013* (2013.01); *A61K 9/2031* (2013.01); *A61P 31/04* (2018.01)

(58) Field of Classification Search
None
See application file for complete search history.

(56) References Cited

U.S. PATENT DOCUMENTS

| | | | |
|---|---|---|---|
| 2,438,781 | A | 3/1948 | Kamlet |
| 4,017,592 | A | 4/1977 | Penard et al. |
| 4,678,661 | A | 7/1987 | Gergely et al. |
| 4,690,772 | A | 9/1987 | Tell et al. |
| 4,713,251 | A | 12/1987 | Seighman |
| 4,983,634 | A | 1/1991 | Corby |
| 5,152,915 | A | 10/1992 | Ralston, Jr. et al. |
| 5,456,211 | A | 10/1995 | Stevenson |
| 6,333,054 | B1 | 12/2001 | Rogozinski |
| 6,564,508 | B1 | 5/2003 | Buchan |
| 6,627,207 | B1 | 9/2003 | Petersen |
| 6,764,693 | B1 | 7/2004 | Smith |
| 8,784,900 | B2 | 7/2014 | Northey |
| 10,029,917 | B2 | 7/2018 | Almas et al. |

| | | | |
|---|---|---|---|
| 2006/0014017 | A1 | 1/2006 | Pilotek et al. |
| 2008/0008621 | A1 | 1/2008 | Ikeda et al. |
| 2009/0247485 | A1 | 10/2009 | Ahmed et al. |
| 2009/0258083 | A1 | 10/2009 | Calderon |
| 2010/0112092 | A1 | 5/2010 | Northey |
| 2010/0166807 | A1 | 7/2010 | Williamson |
| 2012/0148516 | A1 | 6/2012 | Abel et al. |
| 2012/0164235 | A1 | 6/2012 | Northey |
| 2013/0215709 | A1 | 8/2013 | Hinderson |
| 2013/0216628 | A1 | 8/2013 | Hinderson et al. |
| 2015/0150906 | A1 | 6/2015 | Hinderson et al. |
| 2015/0150907 | A1 | 6/2015 | Hinderson et al. |
| 2015/0231173 | A1 | 8/2015 | Sampson et al. |
| 2015/0264935 | A1 | 9/2015 | Chang |
| 2016/0271171 | A1 | 9/2016 | Almas |
| 2017/0266227 | A1 | 9/2017 | Almas |
| 2018/0177822 | A1 | 6/2018 | Almås |

(Continued)

FOREIGN PATENT DOCUMENTS

| | | |
|---|---|---|
| CN | 102696676 A | 10/2012 |
| EP | 1829449 A1 | 9/2007 |
| EP | 2937101 A1 | 10/2015 |

(Continued)

OTHER PUBLICATIONS

International Search Report and Written Opinion mailed Jul. 30, 2013, for International Application No. PCT/IB2013/000682, filed Feb. 19, 2013 (7 pages).

Kuroiwa, K, et al., "Augmnenting effect of acetic acid for acidification on bactericidal activity of hypochlorite solution", Lett. Applied Microbiol., 2003, pp. 46-49.

Wang, L.. et al., "Hypochloroous Acid as a Potential Wound Care Agent", J. Burns Wounds, 2007, pp. 65-79.

International Search Report and Written Opinion of the International Searching Authority Searching Authority mailed May 17, 2018 for International Application No. PCT/IB2017/001728 (17 Pages).

Dash, Sukalyan et al. "Oxidation by Permanganate: Synthetic and Mechanistic Aspects," Tetrahedron, vol. 65, 2009, pp. 707-739 (33 Pages).

Boddie, R. L. et al., "Efficacy of Teat Dips Containing a Hypochlorous Acid Germicide Against Experimental Challenge with *Staphylococcus aureus* and *Streptococcus agalactiae*", J. Dairy Sci., 1996, pp. 1683-1688 (6 Pages).

(Continued)

*Primary Examiner* — Brian Gulledge

(74) *Attorney, Agent, or Firm* — Thomas C. Meyers; Sullivan & Worcester LLP

(57) ABSTRACT

The present invention provides new storable and stable disinfectant compositions comprising use of a solid precursor of an oxidized state of chlorine. The component in the device is devoid of stability issues, since the solid precursors are instantly to be dissolved in water or a pharmaceutically acceptable diluent, adjuvant, or carrier, and combined with an activator, e.g. adipic or succinic acid or their salts, optionally combined with a viscosity enhancer, optionally combined with a dye. The main product according to the invention is generated by dissolving effervescent material in the form of tablets or granules, the resulting solutions from dissolution of the effervescent material are useful disinfectants for treating a broad spectrum of pathogenic bacterial and/or viral, fungal, or parasitic pathogens, denoted microbials.

17 Claims, 1 Drawing Sheet

(56) References Cited

U.S. PATENT DOCUMENTS

| | | | | |
|---|---|---|---|---|
| 2021/0259974 A1* | 8/2021 | Schaub | | A61K 9/0009 |
| 2021/0352905 A1* | 11/2021 | Almås | | A01N 59/00 |

FOREIGN PATENT DOCUMENTS

| | | | | |
|---|---|---|---|---|
| JP | 10-87462 | A | 4/1998 | |
| JP | H10309582 | A | 11/1998 | |
| JP | 2003040716 | A | 2/2003 | |
| JP | 2007-126437 | A | 5/2007 | |
| JP | 2007-326050 | A | 12/2007 | |
| JP | 4150533 | B2 | 9/2008 | |
| JP | 2009274950 | A | 11/2009 | |
| JP | 2011056377 | A | 3/2011 | |
| JP | 2011-229833 | A | 11/2011 | |
| JP | 2013515021 | A | 5/2013 | |
| WO | 1994021125 | A1 | 9/1994 | |
| WO | WO-0051434 | A1 * | 9/2000 | A01N 59/00 |
| WO | 2001028336 | A1 | 4/2001 | |
| WO | 200506383 | A2 | 7/2005 | |
| WO | 2006057311 | A1 | 6/2006 | |
| WO | 2011014809 | A1 | 2/2011 | |
| WO | 2012123695 | A2 | 9/2012 | |
| WO | 2013121294 | A1 | 8/2013 | |
| WO | 2015082937 | A2 | 6/2015 | |
| WO | 2017203364 | A1 | 11/2017 | |
| WO | 2018115977 | A1 | 6/2018 | |
| WO | 2020089689 | A1 | 5/2020 | |
| WO | 2020089693 | A1 | 5/2020 | |

OTHER PUBLICATIONS

Schmittinger, P. et al. "Chlorine", Wiley, 2000, pp. 160-164 (7 Pages).

Plaizier-Vercammen, Jacqueline, "Rheological Properties of Laponite XLG, A Synthetic Purified Hectorite", Die Phrmazie: an International Journal of Pharmaceutical Scieces, Govi Veriag Pharmazeutischer Vertag GMBH, DE, vol. 47, No. 11, Nov. 1992, pp. 856-861 (6 Pages).

International Search Report and Written Opinion of the International Searching Authority Mailed Sep. 8, 2017 for International Application No. PCT/IB2021/000757 (17 Pages).

Puttaiah, R., et al, Dental Unit Water Line Treatment with Sodium Hypochlorite and Acetic Acid, Microchemical Journal, 1998, pp. 333-340 (8 Pages).

Akbarzadeh et al, "Liposome: Classification, Preparation, and Application," Nanoscale Res Lett, 2013, 8:102, 9 Pages.

Borkow et al, "Copper, An Ancient Remedy Returning to Fight Microbial, Fungal and Viral Infections," Current Chemical Biology, 2009, 3, 272-278.

Grijaivo et al., "Biodegradable liposome-encapsulated hydrogels for biomedical applications: A marriage of convenience," Biomaterials science 4.4, 2016, pp. 555-574.

Henry, "Experiments on the Quantity of Gases absorbed by Water, at Different Temperatures, under Different Pressures," downloaded from rstl.royalsocietypublishing.org on Jan. 4, 2010, 18 pages.

Mozafari, "Nanoliposomes: Preparation and Analysis," Liposome, Methods in Molecular Biology, vol. 605, pp. 29-50.

Pandey et al., 2013, Biodegradable Polymers for Potential Delivery Systems for Therapeutics, Multifaceted Development and Application of Polymers for Biology, Biomedicine and Nanotechnology, Springer, Berlin, Heidelberg, 169-202.

Setlow, "Spores of Bacillus subtilis: their resistance to and killing by radiation, heat and chemicals," Journal of Applied Microbiology 101, 2006, pp. 514-525.

Chinese Office Action issued in Chinese Application No. 201780042967. 8, date of mailing: Jun. 2, 2021, 18 pages.

European Office Action issued in European Patent Application No. 17847767.5, date of mailing: Apr. 19, 2021, 4 pages.

European Office Action issued in European Patent Application No. 17847769.1, date of mailing: Apr. 30, 2021, 9 pages.

Japanese Office Action and English Translation issued in Japanese Application No. 2019-54872, date of mailing: Apr. 15, 2021, English translation obtained from google translate which can be accessed at https://translate.google.com, 5 pages.

Korean Preliminary Rejection issued in Korean Patent Application No. 10-2018-7037219, date of mailing: Jul. 2021, 4 pages.

Non-Final Office Action issued in U.S. Appl. No. 15/852,767, date of mailing: May 26, 2021, 13 pages.

Notice of Decision issued in Saudi Arabia Application No. 518400529, date of mailing: Jun. 8, 2021, 2 pages.

Office Action issued in Philippines Patent Application No. 1-2018-502506, date of mailing Jun. 9, 2021, 3 pages.

Park, 2005, Effects of Silver Nanoparticles on the Fluidity of Bilayer in Phospholipid Liposome, Colloids and Surfaces Biointerfaces 44.2-3:117-122.

Subsequent Substantive Examination Report issued in Philippines Application No. 1-2018-502506, date of mailing: May 25, 2021, 4 pages.

Indonesian Exam Report Issued in Patent Application No. PID201905970, date of mailing: Aug. 26, 2021, 3 pages.

Romling et al., Biofilm infections, their resilience to therapy and innovative treatment strategies, Journal of Internal Medicine, 272.3, 2012, 541-561.

Non-Final Office Action issued in U.S. Appl. No. 15/852,615, date of mailing, Oct. 19, 2020, 17 pages.

Non-Final Office Action issued in U.S. Appl. No. 15/267,220 date of mailing: Sep. 18, 2020, 56 pages.

Exam Report issued in Philippines Application No. 1-2018-502506, date of mailing: Oct. 28, 2020, 4 pages.

Exam Report issued in Indian Application No. 201817044946, date of mailing: Jul. 6, 2020, 17 pages.

English Translation of the Office Action issued in Eurasian Patent Application No. 201892805, date of mailing: Feb. 19, 2020, 3 pages.

Chinese Office Action and English Translation issued in Chinese Application No. 2017800868745, date of mailing: Oct. 21, 2020, 14 pages.

Notice of Decision issued in Saudi Arabian Application No. 519402147, date of mailing: Jan. 17, 2022, 2 pages.

Japanese Office Action issued in Japanese Application No. 2019-534688, date of mailing: Oct. 12, 2021, 7 pages.

Notice of Decision issued in Saudi Arabian Application No. 518400529, date of mailing: Jun. 8, 2021, 2 pages.

* cited by examiner

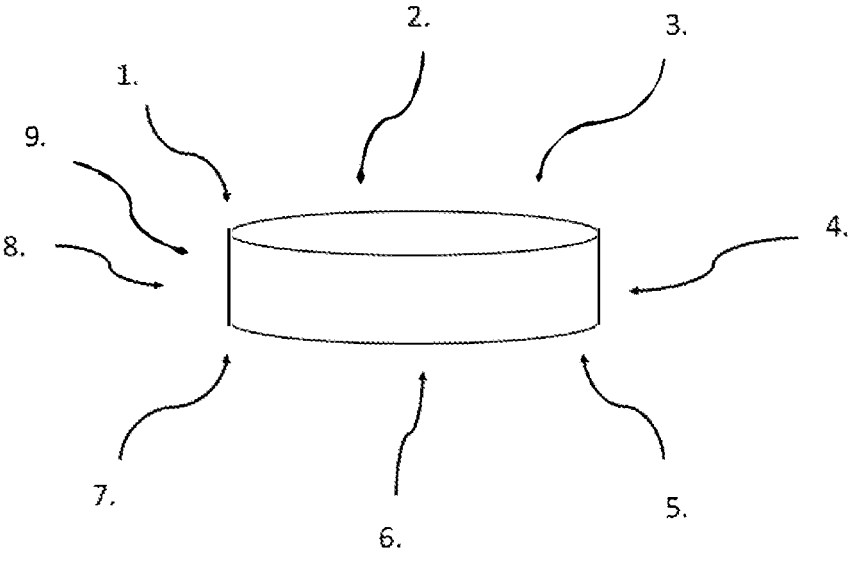

COMPOSITIONS AND METHODS FOR TREATMENT AND PREVENTION OF PATHOGENS

FIELD OF THE INVENTION

The present invention relates generally to compositions comprising combinations of one or more solid precursors of oxidized states of chlorine for the treatment and prevention of pathogens.

BACKGROUND OF THE INVENTION

Microorganisms include bacteria, fungi, archaea, parasites, protozoa and viruses; and are among the earliest known life forms. These types of microorganisms may be either free-living or parasitic.

Free-living microbes, such as bacteria or fungi, have the potential to grow on surfaces or in host organisms, leading to infections in the host organism that may become pathological and possibly lead to illness or death.

Infectious diseases are a leading cause of death worldwide and account for more than 13 million deaths annually, including nearly two-thirds of all childhood mortality. Moreover, antibiotic resistance is increasing and is contributing to morbidity in a broad range of human diseases, including pneumonia, tuberculosis and cholera. Of particular concern is the number of human pathogens developing multidrug resistance to conventional antibiotics. The introduction of new, more potent, derivatives of existing antibiotics provides only temporary solutions, since existing resistance mechanisms rapidly adapt to accommodate the new derivatives (Høiby et al, *Int. J. Antimicrob. Agents* 2010). Although resistant Gram-positive bacteria pose a significant threat, the emergence of multidrug resistant (MDR) strains of common Gram-negative pathogens, such as *Escherichia coli*, are of particular concern. Pan-resistance or extreme drug resistance are now commonly used terms to describe clinically important isolates of *Pseudomonas aeruginosa, Acinetobacter baumannii* and Enterobacteriaceae that are resistant to virtually all antibiotics.

Viruses are also a significant concern in infectious epidemiology. Serious viral outbreaks, many of zoonotic origin, are becoming increasingly common. For example, the SARS (severe acute respiratory syndrome) and MERS (Middle East respiratory syndrome) outbreaks in the early-to-mid 2000s, the H1N1 pandemic in 2009, and the subsequent SARS CoV-2 pandemic in 2020 have focused attention on both treatment and prevention of the spread of these viral pathogens.

Many viruses that infect the respiratory tract are communicated via droplet infection. In that case, respiratory droplets containing virus are expelled by an infected person and picked up by others on direct contact or by contact with surfaces on which the droplets land. Typically, infection proceeds via the binding of the virus to receptors on mucosal or epithelial cells, followed by entry into the nose, eyes, ears, or mouth. In addition, other viruses are transmitted via aerosol particles containing the virus or are air borne. In either case, the virus may survive from hours to days after expression from an infected individual.

Infections can be caused by microorganisms, such as viruses, bacteria, fungi, spores, parasites and combinations thereof as described herein. The viruses can be any virus, including but not limited to adenoviruses, human immunodeficiency virus (HIV), rhinoviruses, flu viruses (e.g., influenza A), and hepatitis (e.g., hepatitis A). The SARS-CoV virus identified in 2002 as the cause of an outbreak of severe acute respiratory syndrome (SARS), and the MERS-CoV virus, identified in 2012 as the cause of Middle East respiratory syndrome (MERS) are examples of pathogenic viruses.

Other problematic microbes include, but are not limited to, rotavirus, respiratory syncytial virus, herpes simplex virus, varicella zoster virus, rubella virus, and other common viruses. Bacterial infections include, for example, infections caused by one or more of *Escherichia coli, Pseudomnoms aeruginosa, Klebsiella pnewnonia, Acinetobacter baumannii, E. coli, Staphylococcus aureus, Bacillus atrophaeus, Streptococcus pyogenes, Salmonella choleraesuis, Shingella dysenteriae, Mycobacterium tuberculosis*, and others. Further, problematic fungi and yeasts can include, for example, one or more of *Candida albicans, Bacillus subtilis, Trichophyton mentagrophytes*, and *Bacillus atrophaeus*.

Conventional compositions and methods for disinfection of inanimate surfaces or contaminated epithelia are not sufficient for the inactivation of all these infectious agents. Current forms of conventional disinfectant compositions and methods may require long and impractical exposure times, or hazardous or corrosive solutions or vapors that cannot be used on expensive instruments or on living tissues, and thus fail to provide ready solutions to growing health risks from drug and disinfectant resistant agents.

It is clear that there is a significant unmet medical need for new ways to treat resistant microbials and viruses, particularly effective against key stages in the microbial entrance into mammalian cells via biological mechanisms, which at the same time are effective outside mammalian biology.

SUMMARY OF THE INVENTION

The present invention relates generally to compositions for elimination of pathogenic viruses, bacteria and other contagions. In a preferred embodiment, the invention comprises on or more solid precursors of oxidized states of chlorine, an acid activator and its salts, and a basic activator. In certain embodiments the acid and base activators are solids. Compositions of the invention also may comprise a viscosity enhancer and/or a dye or a redox-activated dye. Compositions of the invention are formulated as an effervescent powder, tablet or granule. When dissolved in water, the resulting solution provides disinfectants for treating a broad spectrum of bacterial, viral, fungal and parasitic pathogens.

Compositions of the present invention are provided as an effervescent powder, tablet or granule to be dissolved in water or pharmaceutically acceptable diluents, adjuvants or carriers. The oxidized chlorine species are combined with acid and base activators in the tablet, the acid activator acts synergistically with the oxidized state of chlorine. The acid activator may preferably be a carboxylic acid, preferably with a melting point above 20 degrees centigrade and/or salts thereof. Optionally, a tablet as set forth herein may comprise a viscosity enhancer, and/or optionally a dye. Compositions of the invention are useful as disinfectants for treating a broad spectrum of bacterial, viral and/or other pathogens.

In a particular aspect, the present invention provides an antimicrobial composition that includes a solid oxidized chlorine species salt, an acid activator, a base activator, and a pharmaceutically acceptable diluent, adjuvant, or carrier. The solid oxidized chlorine species salt is based on the formula $M^{n+}[Cl(O)_x]_n^{n-}$ where M is an alkali metal, alkaline earth metal or transition metal ion, n is 1 or 2, and x is an integer between 1 and 4, inclusive. The acid activator is based on the formula $RN(COOH)_m$ or its salts, where RN is an organic moiety comprising 1-25 carbon atoms, saturated or unsaturated, optionally substituted with oxygen or hydrogen to form functional groups that cannot be oxidized by the chlorinated species, and m is an integer from 0-10. The base activator is able to react with the acid activator to generate carbon dioxide, and is based on the formula $(M^{n+})_s((H)_tCO_3)_u$, wherein n is 1 or 2, s is 1 or 2, t is 0 or 1, u is 1 or 2, t+s+n is an integer between 1 and 5, inclusive, and M is an alkali metal, an earth alkali metal, or a transition metal.

Preferably the antimicrobial composition comprises a solid oxidized chlorine species salt according to the formula: $M^{n+}[Cl(O)_x]_a^{w-}$ wherein M is an alkali metal, alkaline earth metal or transition metal ion, n, a, and w are each independently 1 or 2, and x is an integer from 1 to 4; an acid activator with the formula: $RN(COOH)_m$ or its salts, where RN is an organic moiety comprising 1-25 carbon atoms, saturated or unsaturated, optionally substituted with oxygen or hydrogen to form functional groups that cannot be oxidized by the chlorinated species, and m is an integer from 0 to 10; a pharmaceutically-acceptable diluent, adjuvant, or carrier; and a base activator that is able to react with the acid activator to generate carbon dioxide, having the formula: $(M'^{z+})_s((H)_tCO_3)_u$, wherein z is 1 or 2, s is 1 or 2, t is 0 or 1, u is 1 or 2, t+s+z is an integer from 1 to 5, and M' is an alkali metal, an earth alkali metal, or a transition metal.

In some embodiments, the oxidized chlorine salt comprises an alkali metal or alkaline earth metal salt of hypochlorous acid. In other embodiments, the oxidized chlorine salt comprises an alkali metal or alkaline earth metal salt of chlorous acid. In certain embodiments, the acid activator is selected from the group consisting of monoacid, diacid, triacid, dioic acid, propionic acid, lactic acid, succinic, glutaric acid, pyruvic acid, citric acid, malic acid, oxaloacetic acid, tartaric acid, adipic acid, fumaric acid, heptanedioic acid, octanedioic acid, a dioic acid containing at least 7 carbon atoms, and derivatives thereof.

In some embodiments, the base activator is chosen from sodium bicarbonate, potassium bicarbonate, sodium carbonate, and potassium carbonate.

In some embodiments, an antimicrobial composition of the invention further comprises a water soluble polyol binder. In some embodiments, the water soluble polyol binder is selected from the group comprising monosaccharides, di-saccharides, polysaccharides or mono- or polyhydroxy acids.

A composition of the invention may further comprise a lubricant. Preferred lubricants include dextrose, lactose, sorbitol, ascorbic acid, sorbitol, mannitol, sodium benzoate, potassium sorbate, polyethylene glycol and derivatives thereof, succinic acid, adipic acid, glutaric acid and clavulanic acid, In some embodiments, a composition of the invention is formulated in an aqueous solution, gel, cream, ointment, or oil. In some embodiments, the dissolved antimicrobial composition has an osmolality in the range of about 0.1 mOsm to about 500 mOsm. In some embodiments, the dissolved composition has a pH between 4 and 8.

Compositions of the invention may further comprise a viscosity-enhancing agent. In some embodiments, the viscosity-enhancing agent comprises a water-soluble gelling agent. In other embodiments, the water-soluble gelling agent is selected from the group consisting of poly acrylic acid, polyethylene glycol, poly(acrylic acid)-acrylamidoalkylpropane sulfonic acid co-polymer, phosphino polycarboxylic acid, and poly(acrylic acid)-acrylamidoalkylpropane and sulfonic acid-sulfonated styrene terpolymers.

Compositions of the invention may additionally comprise a dye including a colour providing a visual indication of the presence an oxidized chlorine compound. In some embodiments, the dye comprises a reduction-oxidation dye. In some embodiments, the colour and intensity of colour of the dye is dependent on an oxidation state of the oxidized chlorine compound.

In some embodiments, the solid components of the antimicrobial composition are contained within an effervescent powder, granules, or tablet.

In a particular aspect, the present invention provides an antimicrobial composition useful in antiviral applications and in antimicrobial applications.

Formulations of the invention are useful for inhalation therapy using an asthma inhaler, nebulizer, or vaporizer to fight viral infections in the upper airways in mammals.

Formulations of the invention are useful for skin or wound prophylaxis or healing.

Formulations of the invention are useful in treatment of mastitis or any other infectious disease in animal or agricultural breeding.

Formulations of the invention are useful in treatment of any infectious disease in aquatic breeding.

Formulations of the invention are useful in treatment of any chemical or biological warfare agents.

In a particular aspect, the present invention provides a method for preparation of effervescent powder, granules and tablets from the antimicrobial compositions. In some embodiments, powder, granules and tablets from antimicrobial compositions are prepared using wet granulation, fluid-bed dryers or vacuum granulators.

In some embodiments, the present invention provides a method for neutralization of chemical or biological warfare agents, using the steps of dissolving the effervescent material in a liquid phase and producing vapour or aerosols in the area or localization of interest.

BRIEF DESCRIPTION OF THE DRAWINGS

FIG. 1 is a schematic illustration showing an exemplary effervescent tablet for dispensing a disinfectant composition according to embodiments of the present invention.

FIG. 1 illustrates an effervescent tablet, prepared from effervescent powder or granules comprising 1. An oxidized chlorine species or salts thereof, 2. an acid activator comprising at least one carboxylic acid functionality 3. optionally a salt of a molecule comprising at least one carboxylic acid functionality, 4. A base activator, 5. optionally a binder, 6. optionally a lubricant, 7. optionally a viscosity enhancer, 8. optionally a dye and 9. optionally sodium chloride to gain osmolality close to blood. The tables can be prepared from the material according to the invention from effervescent powder or granules using wet granulation, fluid-bed dryers, vacuum granulators or any other method suited for tablet production.

DETAILED DESCRIPTION OF THE INVENTION

The present invention relates generally to compositions comprising a combination of a solid and liquid precursor of an oxidized state of chlorine and an activator, e.g., glutaric acid or its salts, as well as one or more additional components. The use of such compositions acts as antimicrobial agents and disinfectants for treatment of a broad spectrum of bacterial and/or viral pathogens on a variety of biotic and abiotic surfaces and environments.

Compositions of the invention may be formulated as solids, for example, in an effervescent powder, tablet or granule. Doing so addresses the issue of reduced shelf life seen with solutions of hypochlorous acid or chlorine dioxide described in the prior art. More specifically, the immediate generation of ready-to-use formulations of an oxidized chlorine species from solid precursors API-P may be performed in an effervescent tablet at the site of use. The effervescent powder, tablet or granule according to the invention is used for dispensing but shows long term, stable storage of the solid compositions consistent with the present invention. In example, the solid precursor of an oxidized state of chlorine and glutaric acid or its salts, a viscosity enhancer, and a dye) and subsequently combine such components to prepare the composition at the desired time of use and on site.

By way of background, chlorine oxides, or oxidized chlorine (also referred to herein as "OC"), comprise a large class of chemical species, and are often found in nature, as well as biological systems in mammals. Chlorine oxides may also exist as neutral compounds or ions, so-called oxyanions. There are several oxyanions of chlorine, in which an oxyanion can assume oxidation states of +1, +3, +5, or +7 with the corresponding anions hypochlorite ($ClO^-$), chlorite ($ClO_2^-$), chlorate ($ClO_3^-$), or perchlorate ($ClO_4^-$). The standard reduction potentials at a low pH of hypochlorous acid (HOCl) is +1.49 and for chlorous acid ($HClO_2$), the standard reduction potential is 1.64, while at basic pH, it is +0.89 and +0.78 respectively. At a pH of 5 to 7, reduction potentials are higher than +1.

Consequently, hypochlorite and chlorite are generally the most useful oxidation states with a potential to kill microbes and parasites at a low pH. In particular, the chloride ion $Cl^-$ is in the most stable oxidation state and is not reactive, nor is it effective as a disinfectant. Chlorate and perchlorate in oxidation states +5, and +7 are more reactive than the lower oxidation states, and may be more difficult to handle.

The hypochlorite ion has the chemical formula $ClO^-$, where chlorine (Cl) is in oxidation state +1, which is a potentially unstable oxidation state since the low-energetic oxidation state of Cl is −1. Both the hypochlorite ion and the chlorite ion combine with a number of cations to form hypochlorites and chlorites, as the salts of these oxidized chlorines. Common examples include sodium hypochlorite (household bleach) and calcium hypochlorite, the main active ingredient of commercial products including bleaching powder, chlorine powder, or chlorinated lime, generally used for water treatment (e.g., swimming pools and the like). The chlorite and hypochlorite ions also referred to herein as the "main chlorine oxides", are useful in various contexts. Sodium chlorite and hypochlorite are strong oxidizing agents, and have been used in water purification, disinfection, as well as bleaching and deodorizing animal products.

Because of sodium hypochlorite producing highly toxic chlorine gas under acidic conditions, commercially available aqueous solutions for household purposes are strongly basic solutions, with the pH adjusted using sodium hydroxide.

Chlorite and hypochlorite are also useful for treatment of various diseases or conditions. For example, chlorite and hypochlorite are useful in the treatment of infections, as described in U.S. Pat. Nos. 4,725,437 and 4,851,222. Chlorite and hypochlorite may also be used to treat HIV, recurrent prostate cancer, cystitis, and chronic active hepatitis C disease (see, for example, McGrath et al., Development of WF10, a novel macrophage-regulating agent, *Curr. Opin. Investig. Drugs*, 3(3):365-73 (March 2002)). Chlorite and hypochlorite have also been described for use in treating oral or periodontal diseases or conditions, such as inflammation of the gingiva (see, for example, U.S. Pat. No. 6,350,438).

Hypochlorous acid (HOCl) is widely used as broad-spectrum household and industrial disinfectant and deodorizer. Hypochlorous acid is a weak acid that is known to rapidly inactivate bacteria, algae, fungus, and other organics, making it an effective agent across a broad range of microorganisms. Additionally, since hypochlorous acid is a weak acid and since people naturally produce certain compounds that allow them to tolerate hypochlorous acid, it is generally not harmful to people. Due to the combination of its biocide properties and its safety profile, hypochlorous acid has been found to have many beneficial uses across many different industries, such as the medical, foodservice, food retail, agricultural, wound care, laboratory, hospitality, dental, or floral industries.

Hypochlorous acid is formed when chlorine dissolves in water. In particular, the acidification of hypochlorite generates hypochlorous acid, where the chlorine atom is in oxidation state +1. Hypochlorous acid exists in equilibrium with chlorine gas in the presence of $Cl^-$, which can escape from solution. The equilibrium is pH-dependent, as illustrated in the following equation (Equation 1):

$$Cl_2 + H_2O \rightleftharpoons HOCl + Cl^- + H^+ \rightleftharpoons ClO^- + Cl^- + 2H^+$$

Increasing pH→ (1)

With reference to the above equation (Equation 1), a high pH drives the reaction to the right, promoting the disproportionation of chlorine into chloride and hypochlorite, whereas a low pH drives the reaction to the left, promoting the release of chlorine gas ($Cl_2$).

Chlorine gas ($Cl_2$) is a toxic and powerful oxidizing agent. One inconvenient property of chlorine gas is the tendency to insert Cl into hydrocarbons, to form mono- or poly-haloalkanes and other chlorinated hydrocarbons in radical reactions (See Barhorst and Kubiak, Environ. Sci. Pollut. Res. (2009) 16, pp 582-589). This is a potential hazard since halogenated hydrocarbons are pollutants and potentially considered carcinogenic. Thus, chlorine gas is not a desired compound to use at higher concentrations in nature or in medical applications. At lower concentrations, chlorine is contributing in the equilibrium to the powerful disinfectant properties of hypochlorous acid with low reasonable risk of medical side effects. However, as long as pH in solutions of hypochlorous acid is controlled and kept in the interval of 4-8, the amount of $Cl_2$ is negligible.

The antimicrobial effect of hypochlorous acid is highly pH dependent and provides the highest level of activity at a pH value of 4 to 5.5, but is also highly active at physiologic pH (7.1-7.5). This means that a hypochlorite solution should ideally be buffered with a weak organic acid and its corresponding metal salt, to have its maximum antimicrobial activity.

In general, formulations containing chlorine oxides are effective antimicrobial agents, with proven antimicrobial and antiprotozoal properties that are useful in disinfectant technologies concerning human and animal health. However, formulations in the prior art have drawbacks. For example, the weak acid HOCl is unstable and impure when produced under conventional conditions. Consequently, there is a need for a more controlled, and immediate preparation processes that can furnish chlorine oxides on site with a stability that permits the intended short-term use.

While the alkalinity of household hypochlorite bleach may be around a pH value of 12, solutions of HOCl are weakly acidic with a pKa value of about 7. Formulations of HOCl in a pH interval around physiological pH 7 are therefore more compatible with medical applications for which bleach is damaging and hazardous to users and to surfaces to which it is applied. Thus, it is of utmost importance to keep pH in the range 4 to 9 to avoid damage to biological tissue or vulnerable surfaces.

In a therapeutic technology, an active pharmaceutical ingredient (also referred to herein as "API"), is understood to be the chemical component or components generating the respective therapeutic effect. A weakness of the formulations in prior art, where hypochlorous acid is the only active API, is the absence of a biocompatible activator and pH-stabilizer that simultaneously acts both as a buffer and as an antimicrobial agent, preferably also in synergy with the API.

Another weakness of prior art technologies is that many of the water solutions in these cases have been produced by electrolysis of isotonic 0.9% $NaCl/H_2O$ (normal saline) and has no buffering capacity because a mixture of a weak biocompatible organic acid and its salt is not present. Further, electrolysis is a rather complicated and sometimes inconvenient method for preparation of the antimicrobial solutions (i.e., in war zones, tourist resorts, or areas of catastrophes or pandemics).

A further weakness of prior art chlorine oxide-based formulations is a lack of stability, based, at least in part, on the fact that chlorine oxides gradually deteriorate and decompose within the first few months of storage, unless stored cold and in the absence of light and oxygen. Thus, pharmaceutical shelf-life stability of solutions of chlorine oxides cannot be achieved at ambient conditions.

Yet another weakness of the chlorine oxide-based formulations in the prior art is the lack of a controlled ionic strength that is adapted to the use of a given formulation. The administration of any given formulation including a chlorine oxide to a mammal ideally requires an ionic strength of 300 mOsm to be iso-osmolal to body fluids, equivalent to about a 150 mM concentration of NaCl.

Hypochlorous acid may be an attractive compound to include in antimicrobial solutions, as neutrophils in the body produce it naturally in pure form in vivo. Further, circulating monocytes, tissue-resident macrophages, and microglial cells in mammals also produce hypochlorous acid to inactivate pathogens within phagocytic vesicles and in the extracellular space around phagocytes in tissues. Thus, hypochlorous acid is a natural biological compound produced by mammals in relatively high concentrations. Activated neutrophils can mobilize their primary granule enzymes to the cell surface. For example, as described by Hirche et al, im J. Immunol. (2005); 174:1557-1565, the enzyme myeloperoxidase (MPO) in activated neutrophils uses hydrogen peroxide ($H_2O_2$) catalyzed by NADPH oxidase to generate HOCl.

Considering the large number of neutrophils that accumulate in inflamed tissues such as lungs of patients with acute respiratory distress syndrome, the concentrations of HOCl that can be of clinical use are of notable physiologic relevance. It is well known in prior art that $5 \times 10^6$ activated neutrophils can generate as much as 100 μM HOCl within 2 hours. Thus, the mammalian biological system may handle concentrations of at least 100 μM HOCl without pathologic consequences.

Another chlorine oxide useful as an API in antimicrobial formulations is chlorine dioxide, wherein the chlorine atom is in oxidation state +3. The main reaction of sodium chlorite is the generation of chlorine dioxide, as illustrated in the following equation (Equation 2):

$$5NaClO_2 + 4HOR \rightleftharpoons 5NaOR + 4ClO_2 + 2H_2O \qquad (2)$$

Referring to the above equation (Equation 2), HOR is usually a mineral acid, such as HCl or citric acid, since a source of protons is needed to convert sodium chlorite, first to chlorous acid, and then to chlorine dioxide, which is a highly water-soluble gas at room temperature.

An advantage of chlorine dioxide is that it cannot generate chlorine gas, $Cl_2$, which is known to react to chlorinated hydrocarbons, e.g. trihalo-methanes, which are toxic environmental pollutants. Another advantage of chlorine dioxide is that the activity as a disinfection agent or stability of its water solutions is not pH dependent.

Chlorine dioxide is generated from sodium chlorite, is approved by FDA under some conditions for disinfecting water, and is used to wash fruits, vegetables, and poultry. Sodium chlorite, $NaClO_2$ is a solid precursor of chlorine dioxide, and is sometimes used in combination with zinc chloride. It also finds application as a component in therapeutic rinses, mouthwashes, toothpastes and gels, mouth sprays, as preservative in eye drops, and in contact lens cleaning solution under the trade name Purite.

Chlorine dioxide is also used for bleaching and stripping of textiles, pulp, and paper. It is also used for disinfection of municipal water treatment plants after conversion to chlorine dioxide. Chlorine dioxide is used for sanitation of the hard surfaces, which come in contact with food and as a wash or rinse for a variety of foods including red meat, poultry, seafood, fruits and vegetables. Because the chlorine oxide compounds are unstable even when properly prepared, there is no measurable residue on food after disinfection. Chlorine dioxide also is used as a teat dip for control of mastitis in dairy cattle.

The U.S. Army Natick Soldier Research, Development and Engineering Center produced a portable "no power required" method of generating chlorine dioxide, known as $ClO_2$ gas, an efficient biocide available for combating contaminants, which range from benign microbes and food pathogens to Category A bioterror agents. In the weeks after the 9/11 attacks when anthrax was sent in letters to public officials, hazardous materials teams used $ClO_2$ to decontaminate the Hart Senate Office Building, and the Brentwood Postal Facility.

In addressing the COVID-19 pandemic, the U.S. Environmental Protection Agency has included $ClO_2$ as an agent that met its criteria for use in environmental measures against the causative corona viruses (see (US EPA, OCSPP (2020 Mar. 13) "List N: Disinfectants for Use against SARS-CoV-2". US EPA Retrieved 2020 Mar. 28, titled "How we know disinfectants should kill the COVID-19 coronavirus", in Chemical & Engineering News, Retrieved 2020 Mar. 31).

However, such formulations in these cases are also subject to the stability issues described above since these technologies also are devoid of a biocompatible activator and stabilizer of a precursor of the chlorine oxide that at the same time acts synergistically in the antimicrobial action of the final formulation.

In summary, the main challenge in prior art of the medical use of solutions of chlorine, in higher oxidation states than −1, is stability, or lack thereof, since these chemical species are in a higher energy state and tend to return to the chloride ion Cl⁻ and will decompose in solution at ambient temperature. This prohibits the required shelf-life stability at ambient conditions of pharmaceutical formulations and medical devices of chlorine oxides. Accordingly, a proper shelf life, as required for medical devices and drugs, is difficult to achieve for solutions of chlorine oxides. This inherent limitation to all oxides of chlorine restricts transport and storage, especially at higher temperature in areas with variable temperature, light humidity, and atmospheric gases.

Effervescent powder, tablet or granules comprise ingredients typically being acids and bases in solid form, which upon mixture with water or a pharmaceutically acceptable carrier produces carbon dioxide. Typical non-limiting examples of acids useful in this reaction are mono-, di- or tri-acids like propionic acid, lactic acid, succinic, glutaric, pyruvic, citric, malic, oxaloacetic acid, tartaric, adipic, fumaric acid or heptane- or octane- or higher dioic acids or derivatives thereof. Citric acid imparts a citrus-like taste to the product. However, acids that cannot be oxidized by chlorine species, e.g., exemplified by, but not limited to, succinic acid, glutaric acid, pyruvic acid, oxaloacetic acid and adipic acid are preferred acids according to the invention.

Typical bases used in the effervescent reaction are sodium bicarbonate, potassium bicarbonate, sodium carbonate, and potassium carbonate. Sodium bicarbonate is very common in effervescent formulas and produces a clear solution after tablet disintegration. Both types of carbonates are used mainly as desiccants, contributing to a dry product.

Water-soluble binders are normally necessary in effervescent tablets to bring the tablet hardness to a point where handling is possible, non-limiting examples of binders are monosaccharides, di-saccharides, polysaccharides or mono- or poly-hydroxy acids. Especially preferred binders are dextrose, lactose, sorbitol, ascorbic acid sorbitol or mannitol. The carboxylic acids mentioned above may also be used as lubricants. The ideal amount of binder is one that makes the tablet hard enough to handle, soft enough to disintegrate and dry enough to be stable. The harder the tablet is, the slower is the disintegration.

Lubrication of effervescent tablets may contribute to suitable and efficient tablet or granule production. Non-limiting examples of water-soluble lubricants are dextrose, lactose, sorbitol, ascorbic acid, sorbitol, mannitol, sodium benzoate, potassium sorbate, polyethylene glycol or derivatives thereof, succinic acid, adipic acid, glutaric acid or clavulanic acid. Tablet presses that use lubrication spray on the punches may eliminate the need of lubrication.

Depending on the product, formulators can use color (artificial or natural), sweeteners (acesulfame potassium, sodium saccharin, aspartame, and sucralose), and flavors (artificial or natural) to enhance a product or to mask taste or smell derived from the active ingredients.

Effervescent tablets and powders are produced in much the same manner as conventional tablets and powders, but production must occur in very low humidity areas which preferably are temperature regulated. Effervescent granulations can be mixed in conventional blending equipment, such as ribbon, twin-cone, and V-type blenders. All equipment should be well grounded and should allow the production to be dry after wash-down.

Wet granulation or fluid-bed dryers of the effervescent base can be attractive production methods. In the latter, the water or binder solution is sprayed onto the effervescent mixture while it is suspended in a stream of hot, dry air.

Vacuum granulators have also been used to make effervescent granulations. In this method, the water or binder solution is sprayed onto the effervescent mixture during blending. Drying occurs by placing the granulation under vacuum and heating it via a thermal jacket.

Advantages of the use of effervescent tablets or granules are many. One is the $CO_2$-driven self-mixing often eliminating the need of tedious shaking procedures. Another advantage is the flexibility in comprising flavors, color or viscosity enhancers into the material. Yet another advantage is the pre-calculation of the amount of precursors and prodrugs of active ingredients in the effervescent material.

The present invention recognizes all these drawbacks associated with prior art compositions using chlorine oxides. In particular, the present invention provides compositions comprising a combination of solid precursors of oxidized states of chlorine (OC) and activators providing a source of protons.

As defined above, in addition to the chlorine oxides, two activators are comprised in the effervescent material. The first activator is a solid carboxylic acid with the formula RN(COOH)m or its salts, where RN is an organic moiety comprising 1-25 carbon atoms saturated and unsaturated optionally substituted with oxygen and hydrogen to form functional groups that cannot be oxidized by the chlorinated species, and m is an integer from 0-10, hereinafter the acid activator.

The second activator is a base being able to react with the acid activator to generate carbon dioxide. The second activator has the general formula $$(M^{n+})_s((H)_t(CO_3)_u,$$

wherein n, s, t and u are integers in the range n=1-2, s=1-2 and t=0-1, u=1-2 with the sum t+s+n=1-5, M is an alkali metal, an earth alkali metal, or a transition metal. Preferred basic activators are sodium or calcium carbonate or sodium bicarbonate.

Such compositions are useful disinfectants for treatment of a broad spectrum of microorganisms. In particular, when the active pharmaceutical ingredient is generated from stable, solid precursors, referred to hereinafter as "API-P" of chlorine oxides at the site of use, the inclusion of the acid activator that simultaneously is reacting with buffering the solution or gel to a biocompatible pH value, the stability issue in prior art is no longer present.

As previously described, the technical solutions in the prior art fail to address how to secure an ionic strength or osmolality of the final antimicrobial solution biocompatible with biological fluids. Even further, the prior art fails to show how to regulate and increase contact time and persistence of the API in region of therapeutic interest, e.g. by regulating rheology and fluidity. Yet still, the prior art fails to provide a relatively simple, yet effective, means of monitoring an oxidation state of the API and visual indication of where the API has been applied during mixing of a disinfectant composition.

Additionally, in some embodiments, compositions of the present invention may further include the use of a viscosity enhancer (also referred to herein as "VE") and/or include a combination of a solid precursor of an oxidized state of chlorine and the activator, e.g., a diacid or its salts.

Another embodiment of the invention is the inclusion of a dye in the formulation, preferably e.g., a redox sensitive dye, with a colour that varies with the oxidation state of the chlorine atom, the advantages of which address the drawbacks described with respect to prior art compositions.

In particular, the preferred compositions of the invention are in a solid form. This eliminates any issues related to shelf-life seen with solutions of hypochlorous acid or chlorine dioxide described in the prior art.

More specifically, the immediate generation of ready to use formulations of the oxidized chlorine species from solid precursors API-P may be released from an effervescent powder, tablet or granules. The effervescent powder, tablet or granules may be used for the preparation, dispensing, and long term, stable storage of prepared compositions consistent with the present invention. In particular, such effervescent tablets or granules described herein may have a number of components required to produce the compositions of the present invention.

In example, the solid precursor of an oxidized state of chlorine and the activator, e.g., succinic, glutaric, adipic or pyruvic acid or their salts, a viscosity enhancer, and a dye is mixed, and subsequently the composition generates at the desired formulation of the disinfectant at the desired time and site of use.

Further, in addition to its antimicrobial properties, the acids exemplified above are attractive because they cannot be oxidized further by oxidizing agents, such as an OC, and because of its endogenic nature in high concentrations biochemically speaking.

Accordingly, the effervescent powder, tablet or granule enables practical use in mixing the components necessary to generate the active solution of the API instantly and at the site of use. It should be noted that, to secure an ionic strength or osmolality of the final antimicrobial solution to adapt to the osmolality on the region of use in the case of medical applications, a precalculated amount of NaCl can be used further in the preparation of effervescent tablets, dependent on the planned use.

A preferred embodiment of the invention is inhalation of selected solutions according to the invention for fighting virus infections un the respiratory systems of mammals. Thus, any nebulizers or inhalators, generally used for the treatment of cystic fibrosis, asthma, chronic obstructive pulmonary disease (COPD) and other respiratory diseases or disorders, converting liquids into aerosols are useful in the present invention. The devices are often employing compressed air or ultrasonic energy to generate atomization of the disinfecting solutions. Pressurized metered dose inhalers (pMDIs), dry powder inhalers (DPIs), slow mist inhalers (SMIs) of any kind, are especially useful, e.g., as described by Prajapati et al. in IJPSR, 2019; Vol. 10(8): 3575-3582. Any electrostatic or non-electrostatic inhalators, e.g., the VORTEX or Pari or Sympotec are also useful to practice the invention.

The effervescent powder, tablet or granules are devoid of stability issues, produces a highly broad-spectrum antimicrobial solution upon mixing of the components, and leaves only biocompatible inactive chemical species already found in human biology or in nature.

As noted above, the activation of the API is effected using an activator, e.g. succinic acid or pyruvic acid, which acts synergistically with oxidized chlorine against microbes, and further maintains acidity in a controlled pH range between 4 and 8. This novel method and the formulations thereof avoids the inherent lack of long-term stability of oxidized chlorine OC in solution (due to its oxidative capacity), since there is no need to store the disinfectant composition as an aqueous solution before use.

Another advantage of the present invention is the option to add other compounds that will aid in application. For example, in wound healing applications, there is a need to increase the viscosity ($\mu$) of the product on the skin to prolong contact time. This is solved by the use of a water-soluble or dissolvable viscosity enhancer (VE) that chemically cannot be oxidized by the API, thereby providing improved regulation of contact time and persistence of the API in a region of therapeutic interest. The VE ensures that the rheology and fluidity is adapted to the respective method and region of disinfection, to generate a solution with full fluidity or a gel. The VE may include, for example, a water-soluble gelling agent such as poly acrylic acid, polyethylene glycol or any other oligomer or polymer that cannot be oxidized by the API.

Additionally, the composition may include one or more dyes, identified in a group of reduction-oxidation dyes (also referred to herein as "ROD" or "RODs"), wherein the color and intensity is dependent on the oxidation state of the oxidized chlorine. It should be noted that, in addition to providing a visual indication (i.e., by way of color) of the oxidation state of the chlorine atom, the RODs further provide an antimicrobial effect of their own. This enhances the synergistic action between the components in the formulation in a novel way. The ROD is able to maintain its color for a period of time sufficient to monitor the oxidative activity of the API, oxidized chlorine, and further provide a visual indication of the region wherein the formulation has been applied, thereby addressing the drawbacks of prior art.

Advantages of the invention, as well as additional inventive features, will be apparent from the description of the invention provided hereinafter.

The oxidized chlorine species denoted OC, having the general formula denoted below:

$$M^{n+}[Cl(O)_x]_n^{n-}$$

wherein M can be any alkali metal, alkaline earth metal or transition metal ion, n is an integer 1-5, x is an integer 1-4, y is an integer 1-2.

If M=Na, n=1, x=1, the API-P is NaOCl 5. If M=Ca, n=2, x=1, the API-P is the solid $Ca(OCl)_2$. If M=Na, n=1, x=2, the API-P is the solid $NaClO_2$. If M=Ca, n=2, x=2, the API-P is the solid $Ca(ClO_2)_2$. In the case x=3 or 4, the API-P generates the more reactive chlorate and perchlorate species.

One non-limiting example is instant generation of hypochlorous acid from sodium-, or calcium di-hypochlorite in the cap 2 according to FIG. 1, in admixture with mono sodium succinate providing a ready-to-use solution of the API hypochlorous acid with a pH between 4 and 6, optionally with a color and a viscosity enhancer.

Another non-limiting example is calcium di-hypochlorite $Ca(OCl)_2$, which is a stable and water-soluble API-P for HOCl, which is being produced and sold in ton-scale as a pool disinfectant. It is rather slowly soluble in water, and only leaves calcium hydroxide, which present in nature and biology, is used in food as E-number E526, and generates HOCl, one of the two the active ingredient in the present invention, which degrades to $Cl^-$ and biocompatible species containing hydrogen and oxygen. However, according to the present invention, the effervescent evolvement of CO2 increases the dissolution rate of $Ca(OCl)_2$, and other solid ingredients significantly.

Another preferred embodiment of the present invention is the solid precursor of oxidized chlorine tetrachloro-decaoxide (TCDO), CAS no. 92047-76-2, known as WF10 or stabilized solutions of OXO-K993, prepared as described by Meuer et al in CA2616008. It can be prepared by combining alkaline or alkaline earth salts of the chlorite ion $ClO_2^-$ with excess oxygen in water.

Thus, one advantage of the present invention is that the solid form precursors API-P in a dry and water-free quality is devoid of pharmaceutical stability issues, thus the present invention solves one of the main technical problems in prior art.

A main aspect of the invention is the combination of the API-P with a molecule comprising a carboxylic acid functionality —COOH, a sulfonic acid functionality —$SO_3H$, a phosphoric acid functionality —$PO_3H$ or a boric acid functionality —$B(OH)_2$, hereinafter defined as the activator of the API-P in the formulation. The activator has the general formula $R_1XO_n(R_2)_m$ wherein the group $R_1$ may be a group comprising 1-10 hydrogenated carbon atoms, optionally substituted with amino, amido, carboxylic or hydroxy groups. The group X may be a carbon, phosphorous or sulfur atom, n and m may be an integer 2 or 3 and $R_2$ may be a proton H, or any alkali metal, alkaline earth metal or transition metal ion. The nature of the substituents in the formula varies according to use and chlorine species, and may be any compound comprising an amino group, e.g., ammonia, an amino acid, e.g., taurine, or a therapeutic drug increasing the synergistic potential of the formulation. The activator may be any combination or mixture of two or more compounds as defined by the general formula $R_1XO_nR_2$.

Preferred non-limiting examples are carboxylic acids $R_3(COOH)_2$, wherein $R_3$ is a linear or branched saturated or unsaturated hydrocarbon chain with 1-24 carbon atoms. Non-limiting examples of activator may be succinic acid, glutaric acid, adipic acid, pyruvic acid, citric acid, tartaric acid, lactic acid, hippuric acid, maleic acid, boric acid, sulfuric acid, phosphoric acid or boric acid Taurine is especially preferred, since it is the endogenic amino acid normally moderating the effect of OC in the body and may be combined with OC to form endogenous N-chloro-amino acids like $ClNH—CH_2CH_2—SO_3H$, which in itself has antibacterial properties.

Succinic acid, glutaric acid and pyruvic acid is even more preferred since they are also endogenic substances, has antibacterial properties, has very low toxicity and forms buffers in admixture with its metal salts, and is used as a non-limiting example in the further description of the invention. In example, Anuj Purohit and Anand Mohan in LWT—Food Science and Technology (2019), 116108596, pp 1-7 reports that pyruvic acid and monosodium succinate a mixture, separately or in a mixture, reduced bacterial log CFU/g ground chicken ground meat with almost log 2.

An advantage of the invention is that the solid multi-component products according to the invention is not hampered with stability issues in a pharmaceutical or medical device setting, regardless of temperature, air, humidity, light, oxygen or other ambient conditions, since the API-Ps are solid and commercially available in large scale.

A further embodiment of the invention is that the API-Ps are not instantly soluble in water using shaking or stirring, but driven by the effervescent evolvement of CO2, they are rapidly dissolved or suspended in the liquid phase, and instantly reaches physiologically acceptable pH and ionic strength in the final solution in combination with succinic acid and/or its salts. The products after disinfection are all endogenic species already present in the human biology or in nature.

Another embodiment is that instant generation of the active disinfection agent according to the invention on site of use will have significant and great influence on the versatility of product applications. It opens for a much more flexible product packaging technology, since the size and amount of the effervescent material in the starting package is freely variable, dependent on use.

Small, stable one-dose single-use, two or three-component packages of the effervescent material will be available, ideally suitable for tourists, catastrophic zones, with military personnel or microbial pandemics. Further, design of large bags, boxes or tanks comprising the API-P is useful in agricultural settings, aquaculture industry or military operations, suitable to disinfect larger areas.

Viscosity Enhancers for Preparations of Viscous Solutions and Gels

A preferred embodiment of present invention is the option to include other compounds in the effervescent powder, tablet, or granules that will aid user-friendliness of the product. For wound healing or skin disinfection applications, there is a need to increase the viscosity ($\mu$) of the product on the skin to prolong contact time. The viscosity enhancer, VE, solves this medical need.

Preferred groups of VE according to the invention are water-soluble gelling agents which the API is not oxidizing since all oxygen-containing functional groups in the VE are in their highest oxidation state. The gelling agents provide prolonged persistence of the API at the area of interest, e.g., mammalian skin.

Examples of gelling agents according to the invention include, but are not limited to, poly acrylic acid (Carbomer), polyethylene glycol or any other oligomer, polymer or block-copolymer thereof. Further, the viscosity enhancer may be selected from, poly(acrylic acid)-acrylamidoalkyl-propane sulfonic acid co-polymers, phosphino polycarboxylic acids and poly(acrylic acid)-acrylamidoalkylpropane or sulfonic acid-sulfonated styrene terpolymers.

A preferred VE is poly acrylic acid, since each monomer has a carboxylic acid functional group. Using this VE will thus add to our preferred pH range of between 4-5.5 since pKa of PAA is 4.5.

Thus, a preferred aspect of the invention is the use of polymers, such as any type of acrylate copolymer, which are well known to those skilled in the art, can function well in the formulation of the invention in concentration ranges 0.01-5%. Acrylate copolymers are homo- and co-polymers of acrylic acid cross-linked with a polyalkenyl polyether. Acrylate copolymers come with a variety in graft density. They vary in terms of their ability to oxidize and how many grafted chains there are per polymer. One possible cross-linker is pentaerytritol, which is very stable, and so it is a good choice for use with the present invention. Polyacrylic acid (PAA) polymers that are known to stabilize formulations of $H_2O_2$, can be used with the present invention (see Schmucker-Castner & Desai, 1999, "Rheology Modification of Hydrogen Peroxide Based Applications Using A Cross-linked PAA polymer," Int J Cosmet Sci 21(5):313-25).

The polymer-stabilized solutions of OC according to the invention have applications in many contexts, e.g., in wound treatment, aseptic packaging, electronics manufacture, and pulp and paper bleaching. The formulation of the API is compatible with formulations as gels or viscous fluids, which may be applied to target surfaces, either inanimate or representative of the infected epithelial mucosal or skin surfaces of infected persons or animals, to ensure prolonged and intimate contact with the necessary levels of API. Non-viscous formulations of the API may also be dispersed into the air in confined spaces as a mist in order to achieve environmental disinfection, or for inhalation purposes for treatment of respiratory diseases.

In example, a concentration of the poly acrylic acid Carbomer has increasing viscosity in the concentration 0.01-0.1%. If desired, it forms regular gels in the concentration range 0.1-1%. To dissolve the VE according to the solution, a mixer, stirrer or sonicator must be used to dissolve it in the microbicidal formulation. The degree of gelling can be even more increased using a biocompatible base, e.g., the pharmaceutical buffer triethanolamine, or other biocompatible amino alcohols.

Antibacterial Redox-Sensitive Antibacterial Dyes as Indicators

A further innovative and, in the context of disinfection technologies, novel aspect of the present invention is the use of reduction-oxidation dyes, for clarity hereinafter denoted ROD, wherein the color and intensity is dependent on the oxidation state of the OC. Even more advantageous, the identified RODs have antimicrobial effect, increasing the antimicrobial lisynergy between constituents according to the invention. If the standard half-cell potential of the ROD has a lower positive value than the OC, the color of the formulation will be maintained as long as the OC is active. Thereby, the color visualizes the region wherein the formulation has been applied and where there is active OC. This is especially advantageous when e.g., the formulation according to the invention is used in treatment of mastitis, where large packs of cattle need to be treated for mastitis; the colored formulation according to the invention visualized which animals have been treated. Further, employment of the opposite type of indicator, where the color appears when the oxidizing power of the OC is vanishing, is also useful Non-limiting examples of suitable dyes useful in the invention, are pH-independent dyes, visible in the presence of an OC. Preferred examples are N-phenylanthranilic acid (violet-red), N-ethoxychrysoidine (cyan), o-dianisidine (red), sodium diphenylamine sulfonate (red-violet), diphenylbenzidine (violet), diphenylamine (violet) and viologen, which is colorless in the presence of an OC, but deep blue in the absence of an OC.

Another preferred example is the pink dye trisodium (4E)-3-oxo-4-[(4-sulfonato-1-naphthyl)hydrazono]naphthalene-2,7-disulfonate, which is more commonly called amaranth (E number 123).

Examples of pH-dependent dyes that are deep blue in the presence of an active OC, but colorless in the absence of the OD are sodium 2,6-Dibromophenol-indophenol or Sodium 2,6-Dichlorophenol-indophenol, sodium o-cresol indophenol, thionine (syn. Lauth's violet), methylene blue, Gentian Violet, indigotetrasulfonic acid, indigo carmine (syn. Indigo-disulfonic acid), indigomono sulfonic acid. Examples of dyes that are red or red-violet in the presence of an OC are phenosafranine, Safranin T, neutral red and dialkyl-p-phenylenediamine (SPD, red violet).

Many of these dyes have inherent antibacterial effects, i.e., methylene blue (MB) and Gentian Violet (GV), and combinations of them have been used as antibacterial dyes in foams in wound dressings in combination with polymers like polyvinyl alcohol or polyurethane, e.g., as described by Edwards in Advances in Wound Care (2016), 5, pp 11-19.

A particularly useful class of dyes useful in the present invention is microbial phenazines, which are pigmented, redox-active, nitrogenous aromatic compounds with metabolic, ecological and evolutionary significance, see e.g. Chincholkar, S. & Thomashow, L. *Microbial Phenazines: Biosynthesis, Agriculture and Health* (eds Chincholkar, S. & Thomashow, L.) 1-243 (Springer, 2014). All these distinctive features make them attractive microbial metabolites, useful as dyes in drug formulations. Reports of over 100 natural and 6000 synthetic phenazines to date exhibiting promising bioactivities including antimicrobial, anticancer, anti-parasitic, and insecticidal and biocontrol properties are available.

An even more attractive class of phenazines include the bis-N-oxide phenazines, with even stronger antimicrobial properties than their parent phenazines. Most of these compounds are natural compounds produced by bacteria, and are hetero-aromatic N-oxidized compounds, hereinafter denoted HANOX. In addition to being redox dyes, RODS, the HANOX compounds are useful in the present invention because their color is dependent on the oxidation state of the OC. At the same time, HANOX in prior art show to possess broad-spectrum anti-microbial activity, e.g., as described by Leimgruber et al in U.S. Pat. No. 3,822,265.

Further, the phenazine derivatives provided by U.S. Pat. No. 3,822,265 have a broad-spectrum fungicide activity. In particular, they demonstrated a high activity against a wide variety of bacterial, yeasts and fungi such as *Streptococcus agalactiae, Staphylococcus aureus, Escherichia coli, Corynebacterium pyogenes, Moraxella bovis, Pseudomnoms aeruginosa, Candida albicans* and *Microsporum canis*. Thus, the phenazine derivatives are particularly useful in the treatment of animal diseases of microbial origin in agriculture.

A surprising finding with these derivatives is their lack of injurious effects to the body tissue under the conditions of use, making them particularly suitable for topical application, preferably employed in amount ranging from 0.05 percent to 1.0 percent by weight of the composition.

They are of particular value in topical applications, e.g., in solid or gel formulations including finely divided powders and granular materials and in liquid formulations including solutions, suspensions, concentrations, tinctures, slurries and aerosols, creams, gels, jellies, ointments and pastes.

An even more preferred group of HANOX, useful in the present invention, is described by Viktorsson et al in WO2015063516A2 and WO2018109504A1. This technology describes RODs possessing red-ox properties and broad-spectrum antimicrobial properties. As described by Viktorsson et al in Bioorg. Med. Chem. (2017) 25, pp 2285-2293, this specific class of HANOX is especially attractive since they show lower toxicity in mammals compared to the compounds described in U.S. Pat. No. 3,822, 265, and may be used with low risk of toxic reactions in the hos of the infection.

Methylene blue is another particularly preferred dye useful in the invention since FDA has approved it as an excipient in drug formulations and it has antibacterial properties and its effects as a therapeutic agents can be enhanced using photodynamic therapy.

Effervescent Tablets Useful in the Invention

FIG. 1 is a schematic illustration showing a schematic, non-limiting and exemplary effervescent tablet for instant generation of a disinfectant solution of the API with excipients in a water solution according to the embodiments and methods of the present invention.

Effervescent tablets are in use in different medical, domestic and agricultural applications. In many of these applications, the antimicrobial solutions generated from the effervescent material are useful in the present invention and may be generated in dual- or multi-chamber bottles, bags, syringes, inhalators, hand disinfection devices, spay bottles or flasks, or tanks, constructed of hard or soft materials, e.g., plastic, rubber, water-proof paper, or metal. The therapeutic formulation in can be easily activated bedside from the device, in the field or in domestic setting, without complicated mixing procedures, and can be stored at ambient temperatures. It can be combined with automated dispensing systems, easily labelled, automatically charted via barcoding.

The effervescent tablet according to the invention is composed of a precalculated amount of components and may be designed to eliminate mixing errors, to avoid undesired exposure to patients and personnel, and meets the Joint Commission and USO 797 guidelines.

Use of the Invention for Antimicrobial Purposes with Photodynamic Therapy

Bacterial elimination using antimicrobial photodynamic therapy (aPDT) has been shown using the alternative therapeutic modality in peri-implantitis treatment. In Photo diagnosis and Photodynamic Therapy (2019), 25, pp 7-16, Huang et al described dose-dependent and pH-dependent bactericidal effects of methylene blue (MB)-mediated aPDT at eliminating Gram-negative (*P. gingivalis* and *A. actinomycetemcomitans*) and Gram-positive (*S. mutans*) bacteria on sandblasting, large-grit and acid-etching (SLA)-pretreated titanium alloy. However, the test formulations did not comprise an OC to enhance the therapeutic effect even further.

Thus, another preferred embodiment of the present innovative formulation comprising an OC, succinic acid or its salt, optionally a viscosity enhancer, is the inclusion of a ROD exemplified by methylene blue for the use of photodynamic therapy, e.g., to improve wound healing or bacterial infections in mammals. In this case, the site of administration of the product according to the present invention can be irradiated with light with a wavelength adapted to generation of the photodynamic effect of the dye.

In Photo diagnosis Photodyn. Ther. (2018), 23, pp 347-352, Souza et al used photodynamic therapy to show antimicrobial activity of hypochlorite solutions and reciprocating instrumentation associated with photodynamic therapy on root canals infected with *Enterococcus faecalis*. However, the test solutions were devoid of an antibacterial dye. These technologies are included in the present invention by reference.

Use of the Invention in Agriculture

In agriculture, especially in animal farms, many kinds of infectious diseases caused by bacteria, viruses and fungi affect the daily operation of the farm and affects the costs in running the facilities. In these settings, designed formulations according to the invention act therapeutically or prophylactically, and are especially useful in skin infections.

One important example is mastitis in cattle, which costs the US dairy industry about 1.7-2 billion USD each year. Effective and environmentally friendly treatment of mastitis has proven difficult, since milk from cows, having received long-term antibiotics is not marketable until the residual drugs have left the system. No vaccines are effective since the infection in the udder and teats of the cow is remote from the animal's main blood stream. To mark cows having received treatment, dairy workers apply strips of tape to alert and mark treated cattle.

Thus, a preferred aspect of the present invention is treatment of mastitis using a gel or viscous solution comprising an OC, succinic acid or its salt or other preferred acid activators or their salts as listed above the viscosity enhancer VE and a ROD exemplified by methylene blue. The colored gel stays on the area of the udder and teats, succinic acid has the ability to penetrate into the skin of the teats, and the color makes use of strips of tape unnecessary. Additionally, the applied gel can be irradiated using light with suitable wavelength to increase the therapeutic effect of the gel. In this case, steps 1-4 and step 6 is performed to yield the instant formulation of use.

Use of the Invention in Aquaculture

Water quality is a prerequisite for a successful culture of aquatic animals, exemplified by fish, oysters, prawns and shrimps. Open water systems often bring organisms like virus, bacteria, lice, protozoa, fungal pathogens, algae and parasites. Common virus infections that lead to high mortality in aquatic species attractive for food production are Koi Herpes Virus Disease, Pancreas disease (PD) and infectious salmon anemia (ISA). Proper water quality or sufficient quantity of pure water is most often not available. The breeding installations in prior art often has no means of hindering these infectious species to approach and effect the breeding species. Further, once infected, there is no efficient cure to provide efficient therapy against these diseases.

A preferred embodiment of the oxidized chlorine species OC according to the present invention is effective treatment of all these infections and harmful organisms and cells. The instant formulations of the OC are highly effective in controlling these waterborne pathogens. In example, chlorine dioxide is a broad-spectrum biocide effective to solve the defined problems in the prior art. The formulations in the present invention are even employed in special tanks to repeatedly treat e.g., bred salmon without harming the fish gills or any other parts of the bred species, while having a destructive effect on the microorganisms causing the disease. In these applications, the preparations sequence wherein the API-P is $NaOClO_2$ or $Ca(OClO_2)_2$ is mixed into the effervescent tablet with a precalculated amount of succinic acid in step 1-3 is used.

Anti-Warfare Applications of the Invention

Another preferred embodiment of the oxidized chlorine species OC according to the present invention is reduction or elimination of warfare agents like nerve gases like the G-series, exemplified by GA, GB (sarin), GD (soman), GF (cyclosarin), GV, the V-series exemplified by VE, VG, VM, VR, and VX, Novichoc, carbamates, insectides, protein toxins like ricin, or biological warfare bacteria, virus or fungi.

All these species have the common feature that they may be oxidized by the oxidized chlorine species according to the present invention. In example, the nerve gas GD or soman has a halogenated phosphorous group that can be oxidized to harmless species by oxidized chlorinated species, as described by Xu et al in E3S Web of Conferences 267, 02043 (2021), pp. 1-6.

However, in this example, an unstable solution of hypochlorous acid was used. The stability problem has been solved according to the invention by using solid effervescent material as an instant precursor to the reactive solution.

An example of anti-warfare use of the produced solution in the present invention is the production of a mist or fog of oxidizing aerosol droplets that may stay in rooms or outdoor for a long period of time to protect living organisms in the area or localization from the warfare agent.

Antiviral Use of the Invention

The methods disclosed herein also permit improved methods of exposure of contaminated surfaces, equipment, e.g., medical equipment, any furniture surfaces, doorknobs, devices, clothing or personnel to disinfectant formulations employing misting or vaporization of the API into confined spaces. This is possible because the degradation status and quality of the disinfectant formulation is known, since it has not been stored as a solution, but is freshly prepared at site of interest from solid precursors.

This procedure ensures dispersion of the active agents into crevices and microenvironments, even onto personnel who are suspected of having been contaminated by infectious tissues or bodily fluids. Vaporization of these formulations may enable beneficial therapeutic or prophylactic impacts on resistant viral, bacterial or fungal infections.

Kim et al in Laryngoscope (2008), 118, pp 1862-1867, studied effects of a low concentration hypochlorous acid for nasal irrigation solution on bacteria, fungi, and virus. The formulations were also used in vitro against human rhinovirus (HRV) in nasal epithelial cells with significant virus-killing effect. Similar formulations were used with good effects against avian influenza virus through in vitro experiment as described by Hakim et al in J. Vet. Med. Sci. (2015), 77, pp 211-215.

Hypochlorous acid has also been used clinically in upper airway mucosa in rhinitis patients. Cho et al reported improved Outcomes after low-concentration hypochlorous acid after nasal irrigation in pediatric chronic sinusitis in Laryngoscope (2016), 126:791-795. To the best of our knowledge, similar formulations have not been used in prior art to treat other parts of respiratory system in mammals.

In U.S. Pat. No. 10,342,825 B by Robert Northey, a low pH antimicrobial solution comprising from 5 mg/L to 200 mg/L hypochlorous acid and water, wherein the solution has a pH of 5.6, stabilized by a phosphate buffer. The solutions may be vaporized using nebulizers for distribution on surfaces and tissue. However, a weakness the formulations used in prior art is the same as described above.

In WO 2019/222768 by Terry, a method for inactivating an infectious agent that is a resistant virus, a cancer-causing virus, a chemically resistant non-enveloped virus, or an infectious agent present in a mucous membrane or epithelial surface. The formulation comprises an infectious agent with a non-buffered, electrolyzed, hypohalous acid composition. However, also in this case, a weakness the formulations used herein is the same as defined above.

Many of the problems in prior art have now been solved using the present invention. For the first time, OC has now been combined with an activator from solid precursors and NaCl for maintaining biological osmolality for the antiviral use of the resulting formulations.

The exposures can be affected without concerns for toxicity or corrosiveness which accompany prior methods of inactivation of highly contagious and resistant infectious agent types. A preferred embodiment is the eradicating, minimizing, or preventing progression of a viral infection in the upper airways, with the result that the immune system has time to mount an antibody response to the virus.

Thus, systems and methods of the invention provide oxidized chlorine, OC, as a means of treating viral infection in the respiratory tract. Compositions of the invention are capable of treating SARS, MERS and other infections, including but not limited to, SARS CoV-2 infections. This has now for the first time been facilitated through the instant precursors of the API combined with the effervescent tablet according to the invention, since there is no need to evaluate the lack of activity of a solution that has been stored at ambient conditions.

Particularly, inhalable hypochlorous acid formulations of OC; an activator, e.g., succinic acid or pyruvic acid; an excipient regulating the rheology of the final solution; an osmolality-regulating agent, e.g., sodium chloride—such instant formulations can now be prepared on site, along with methods of delivery via a nebulizer, such as soft mist inhalers, jet nebulizers, ultrasonic wave nebulizers, and vibrating mesh nebulizers may be used. Upon use, inhalers and nebulizers aerosolize compositions of the invention for delivery via inhalation.

Formulations that may be used to produce aerosols may be provided in dry powder form, solution, or suspension form. Fine droplets, sprays, and aerosols can be delivered by an intranasal or intrapulmonary pump dispenser or squeeze bottle. Compositions can also be inhaled via an inhaler, such as a metered dose inhaler or a dry powder inhaler. Compositions can also be inhaled via a nebulizer, such an ultrasonic wave nebulizer, providing compositions of OC and succinic acid directly to respiratory tracts via inhalable formulations. This prevents and treats infections of the respiratory system caused by viruses as well as other microbes. According to the invention, formulations as described herein are safe and effective for the prevention and treatment of viral infections.

Compositions of the invention may also include a pharmaceutically acceptable carrier, such as a diluent, to facilitate delivery to the respiratory mucosa. The carrier might be an aqueous carrier such as water or saline. The composition may be isotonic, having the same osmotic pressure as blood and lacrimal fluid. Suitable non-toxic pharmaceutically acceptable carriers are known to those skilled in the art. Various carriers may be particularly suited to different formulations of the composition, for example whether it is to be used as drops or as a spray, a suspension, or another form for pulmonary delivery.

Formulations for inhalation may be provided in dry powder form, solution, or suspension form. The composition can be delivered by various devices known in the art for administering drops, droplets, and sprays. The composition can be delivered by a dropper, pipet, or dispenser. Fine droplets, sprays, and aerosols can be delivered by an intranasal or intrapulmonary pump dispenser or squeeze bottle.

Intranasal delivery may be provided via a nasal spray device. Accordingly, the formulations according to the invention may be designed as a nasal spray. The nasal spray is insufflated into the nose and is delivered to the respiratory tract.

Soft mist inhalers use mechanical energy stored in a spring by user-actuation to pressurize a liquid container, causing the contained-liquid to spray out of a nozzle for inhalation in the form of a soft mist. Soft mist inhalers do not rely on gas propellant or electrical power for operation. The average droplet size in soft mist inhalers is about 5.8 micrometers.

Jet nebulizers are the most commonly used and may be referred to as atomizers. Jet nebulizers use a compressed gas (e.g., air or oxygen) to aerosolize a liquid medicine when released there through at high velocity. The resulting aerosolized droplets of therapeutic solution or suspension are then inhaled by a user for treatment. The compressed gas may be pre-compressed in a storage container or may be compressed on-demand by a compressor in the nebulizer.

Ultrasonic wave nebulizers rely on an electronic oscillator to generate a high frequency ultrasonic wave that, when directed through a reservoir of a therapeutic suspension of solution, aerosolized the medicine for inhalation.

Vibrating mesh nebulizers use the vibration of a membrane having thousands of holes at the top of the liquid reservoir to aerosolize a fine-droplet mist for inhalation. Vibrating mesh nebulizers avoid some of the drawbacks of ultrasonic wave nebulizers, offering more efficient generation of aerosols with reduced treatment times and less heating of the liquid being nebulized.

Treatment of a viral infection is achieved using a synergistic composition of glutaric acid and hypochlorous acid. The glutaric acid component is particularly effective for penetrating into tissues, while the hypochlorous acid is particularly effective for treating infection on the outer surface of tissue. As described above, these compositions are effective for treating the respiratory tract and for preventing respiratory infection.

The disclosed compositions are particularly effective because balancing the concentrations of hypochlorous acid and glutaric acid with NaCl allows safe treatment of viruses. The precise balance depends on the formulation, the treatment site, and even the desired amount of surface penetration. The hypochlorous acid can be present in about 5 ppm up to about 1000 ppm or more. Different uses, different delivery methods, and types of tissue may require higher or lower concentrations. The glutaric acid may be present at about 0.1-% up to about 5.0% or more, and preferably about 1.0%. By balancing the two components, the composition can have the dual effect of treating at the surface and beneath the surface of the tissue to which it is applied.

In the case that the OC is hypochlorous acid HOCl, an instant composition having a concentration of about 15-200 ppm of the OC is normally sufficient for treatment of infected lungs. In the case that the OC is chlorine dioxide $OCl_2$, a concentration of 0.1-5 ppm is usually sufficient.

In some cases, to fully destroy the virus or to prevent the virus from entering the respiratory tract, the composition should be in contact with it for a prolonged period, ranging from a few seconds, to several minutes, to an hour or more. Accordingly, in certain embodiments, the composition is in the form of a gel, which allows longer contact times with the infection site.

The use of the composition in combination with a known antiviral treatment may increase the efficacy of the compositions. In some embodiments, methods of the invention further comprise administration (simultaneously or sequentially with compositions of the invention) of one or more doses of an antiviral substance. These may include, but are not limited to, acyclovir, adefovir, adamantine, boceprevir, brivudine, cidofovir, emtricitabine, entecavir, famciclovir, fomivirsen, foscarnet, ganciclovir, lamivudine, penciclovir, telaprevir, telbivudine, tenofovir, valacyclovir, valganciclovir, vidarabine, m2 inhibitors, neuraminidase inhibitors, interferons, ribavirin, nucleoside reverse transcriptase inhibitors, non-nucleoside reverse transcriptase inhibitors, non-structural protein 5a (ns5a) inhibitors, chemokine receptor antagonist, integrase strand transfer inhibitors, protease inhibitors, and purine nucleosides.

The compositions are also useful in combination with a known antimicrobial treatment.

In some embodiments, methods of the invention further comprise administration (simultaneously or sequentially with compositions of the invention) of one or more doses of an antibiotic substance, including, but not limited to, ciprofloxacin, beta-lactam antibiotics like ampicillin or carbapenems, azithromycin, cephalosporin, doxycycline, fusidic acid, gentamycin, linezolid, levofloxacin, norfloxacin, ofloxacin, rifampin, tetracycline, tobramycin, vancomycin, amikacin, ceftazidime, cefepime, trimethoprim/sulfamethoxazole, piperacillin/tazobactam, aztreonam, meropenem, colistin, or chloramphenicol.

In some embodiments, methods of the invention further comprise administration of one or more doses of an antibiotic substance from an antibiotic class including, but not limited to, aminoglycosides, carbacephem, carbapenems, first generation cephalosporins, second generation cephalosporins, third generation cephalosporins, fourth generation cephalosporins, glycopeptides, macrolides, monobactam, penicillins, polypeptides, quinolones, sulfonamides, tetracyclines, lincosamides, and oxazolidinones. In some embodiments, methods of the invention comprise administration of a nonantibiotic antimicrobial substance, including but not limited to sertraline, racemic and stereoisomeric forms of thioridazine, benzoyl peroxide, taurolidine, and hexetidine.

The dosing regimen of the composition may include the amount, frequency, and duration of exposure to the composition. The dosing regimen may depend on the severity of the infection, or on a regimen prescribed for treatment or for prevention of the viral infection.

The composition may be administered in a single daily dose or in multiple doses, e.g., 2, 3, 4, or more doses, per day. The subject receiving the composition may be exposed to the composition for periods of hours or of minutes. The duration of exposure may depend on the frequency, amount, or even of the severity of the infection.

The total daily amount of API formed in the instant solution from the solid precursors may be in the range 0.01-1000 mg, depending on the nature of the OC. The actual dosage may vary depending upon the specific composition administered, the mode of administration, and other factors known in the art.

The composition may be administered to any member of the respiratory tract, such as the respiratory epithelium, nasal cavity, nasal epithelium, pharynx, esophagus, larynx, epiglottis, trachea, carina, bronchi, bronchioles, or the lungs. Administering the composition to the respiratory tract treats prevents any disease or disorder that is transmitted by a virus.

In certain other embodiments, the compositions of the invention can be used to disinfect whole rooms, facilities medical devices and surgical instruments, for example. Supplies of medical devices are often initially sterile but may require additional or subsequent cleaning and disinfection or sterilization. In particular, sterilization or disinfection of reusable medical devices prior to reuse employing any known technique is especially important. Compositions can be applied to the medical device using. For example, the composition can be applied by wiping or spreading it onto the surface of the device, by spraying an aerosol or mist form of the composition onto the device, by dipping the device into a vessel containing a volume of the composition, or by placing the device into a flow of the composition such as from a faucet. Additionally, or alternatively, medical devices and surgical instruments may also be stored submerged in the composition and removed at the time of use.

In summary, the disinfection efficacy of the complete instant formulation according to the invention have been found to be greater than the efficacy of its components alone, as known in prior art. The differences in performance are easily observable across a wide range of concentrations.

Additionally, since both oxidized chlorine chemical species and glutaric acid is toxic at high concentrations, the prior art has taught away from the use of these agents on skin or other tissue, except in trace amounts. Thus, the present invention is surprisingly safe and effective when used in a controlled manner as described above.

Some of the disclosed compositions contain glutaric acid at 2% or greater, and when in combination with the OC have proven to be safe and effective for treating skin and other tissues. The OC in these compositions has been found to have a modulating effect of the glutaric acid.

This allows the compositions to take advantage of the disinfecting properties of glutaric acid without causing harm to the tissue.

General Procedure for Preparation of Dry, Solid Mixtures of API-P and NaCl for Inclusion in Precalculated Amount in the Effervescent Tablet Example 1. Preparation of OC Powder and Effervescent Powder Formulations a) Preparation of Powdered $Ca(OCl)_2$ as Part of the Powder/ Effervescent Powder/Effervescent Tablet/Granules Composition I. 100 g of calcium hypochlorite granules were introduced, successively, into a ceramic mortar (Porsgrunn Porselen, Norway). The granules were powdered in several rounds with the mortar and a pestle. The powder was sieved, respectively, in ≤75 μm, ≤150 μm, ≤250 μm, ≤355 μm and ≤500 μm masks (Retsch, Haan, Germany). The powdered material was stored in various containers of the following material: PET, amber glass, PE.

II. 100 g of calcium hypochlorite granules for dry grinding were introduced, successively, into a Retsch mortar grinder (Haan Germany). Final fineness of the powder was adjusted, respectively, to ≤75 μm, ≤150 μm, ≤250 μm, ≤355 μm and ≤500 μm.

III. 100 g of calcium hypochlorite granules for dry grinding were introduced, successively, into a Retsch drum mill (Haan Germany). Final fineness of the powder was adjusted, respectively, to ≤75 μm, ≤150 μm, ≤250 μm, ≤355 μm and ≤500 μm.

b) Preparation of Powdered Sodium Hydroxide (NaOH) as Part of the Powder/Effervescent Powder/Effervescent Tablet/Granules Composition I. 100 g of sodium hydroxide pellets were introduced, successively, into a ceramic mortar (Porsgrunn Porselen, Norway). The granules were powdered in several rounds with the mortar and a pestle. The powder was sieved, respectively, in ≤150 μm, ≤250 μm, 355 μm and ≤500 μm masks (Retsch, Haan, Germany). The powdered material was stored in various containers of the following material: PET, amber glass, PE.

II. 100 g of sodium hydroxide pellets for dry grinding were introduced, successively, into a Retsch mortar grinder (Haan Germany). Final fineness of the powder was adjusted, respectively, to ≤150 μm, ≤250 μm, ≤355 μm and ≤500 μm.

III. 100 g of sodium hydroxide pellets for dry grinding were introduced, successively, into a Retsch drum mill (Haan Germany). Final fineness of the powder was adjusted, respectively, to ≤150 μm, ≤250 μm, ≤355 μm and ≤500 μm.

c) Preparation of Powder Formulation with Glutaric Acid as an Acid Activator 1.65 g of glutaric acid was mixed, volumetrically, with 0.33 g of powdered NaOH (particle sizes ≤150 μm, ≤250 μm, 355 μm, ≤500 μm) and 102.0 mg of powdered $Ca(OCl)_2$ (particle sizes ≤150 μm, ≤250 μm, ≤355 μm, ≤500 μm) to gain a precalculated powder formulation readily available to mix with water to release a stabilized hypochlorous acid solution.

d) Preparation of Powder Formulation with Glutaric Acid as an Acid Activator 1.48 g of succinic acid was mixed, volumetrically, with 0.35 g of powdered NaOH (particle sizes ≤150 μm, ≤250 μm, ≤355 μm, ≤500 μm) and 102.8 mg of powdered $Ca(OCl)_2$ (particle sizes ≤150 μm, ≤250 μm, ≤355 μm, ≤500 μm) to gain a precalculated powder formulation readily available to mix with water to release a stabilized hypochlorous acid solution.

e) Preparation of Effervescent Powder Formulation with Glutaric Acid as an Acid Activator 3.30 g of glutaric acid was mixed, volumetrically, with 1.60 g of sodium bicarbonate and 220.9 mg of powdered $Ca(OCl)_2$ (particle sizes ≤150 μm, ≤250 μm, ≤355 μm, ≤500 μm) to gain a precalculated effervescent powder formulation readily available to mix with water, to release a stabilized hypochlorous acid solution. The effervescence time was determined by dissolving the effervescent powder in a beaker containing 100 ml of distilled water at 20° C. The effervescence time was measured with a chronometer; the end of effervescence was reached when the solution became limpid and was without any particles.

f) Preparation of Effervescent Powder Formulation with Succinic Acid as an Acid Activator 2.95 g of succinic acid was mixed, volumetrically, with 1.61 g of sodium bicarbonate and 221.9 mg of powdered $Ca(OCl)_2$ (particle sizes ≤150 μm, ≤250 μm, ≤355 μm, ≤500 μm) to gain a precalculated effervescent powder formulation readily available to mix with water, to release a stabilized hypochlorous acid solution. The effervescence time was determined by dissolving the effervescent powder in a beaker containing 100 ml of distilled water at 20° C. The effervescence time was measured with a chronometer; the end of effervescence was reached when the solution became limpid and was without any particles.

Example 2. Powder Flow Determination 100 g of powdered calcium hypochlorite of sizes ≤355 μm and ≤500 μm was added, respectively, into a dry funnel (Ø110 mm, diameter of the outflow opening=15 mm), whose bottom opening has been blocked by a plastic cover. The bottom opening of the funnel was unblocked to measure the time needed for the entire sample to flow out. The flowability of particle sizes ≤355 μm and ≤500 μm is, respectively, 35.7 g/s and 37.4 g/s. The angle of repose was calculated as 29.5° and 26.8° for particle sizes 355 μm and ≤500 μm, respectively.

Example 3. Dissolving Time of Powdered Calcium Hypochlorite, Particle Sizes ≤250 μm, ≤355 μm and ≤500 μm I. 58±4 mg of all sizes of the powdered material was, respectively, dissolved in 100 mL 0.25% wt. acetic acid/acetate buffer. Particle size ≤250 μm dissolved within 10 seconds, ≤355 μm within 15 seconds and ≤500 μm within one minute and 25 seconds at 2500 rpm.

II. 58±4 mg of all sizes of the powdered material was, respectively, dissolved in 100 mL 3.0% wt. acetic acid/acetate buffer. Particle size ≤250 μm dissolved within 10 seconds, ≤355 μm within 25 seconds and ≤500 μm within 25 seconds at 2500 rpm.

III. 570±40 mg of all sizes of the powdered material was, respectively, dissolved in 100 mL 0.25% wt. acetic acid/acetate buffer. Particle size ≤250 μm dissolved within 15 seconds, ≤355 μm within 45 seconds and ≤500 μm within one minute and 35 seconds at 2500 rpm.

IV. 570±40 mg of all sizes of the powdered material was, respectively, dissolved in 100 mL 3.0% wt. acetic acid/acetate buffer. Repeated with 3.0% acetic acid/acetate buffer. Particle size ≤250 μm dissolved within 15 seconds, ≤355 μm within 15 seconds and ≤500 μm within 20 seconds at 2500 rpm.

Example 4. Preparation of Effervescent Tablets a) Preparation of Granulated Material Molecular weights of preferred carboxylic acids and bases useful according to the present invention are: Sodium hypochlorite (mw: 74.44 g/mol), calcium hypochlorite (mw: 142.98 g/mol), sodium chlorite (mw: 90.44 g/mol), calcium chlorite (mw: 157.89 g/mol), succinic acid (mw: 60.05 g/mol), pyruvic acid (88.06 g/mol), glutaric acid (132.12 g/mol), citric acid (192.12 g/mol), malic acid (134.09 g/mol), oxaloacetic acid (132.07 g/mol), tartaric acid (150.09 g/mol), adipic acid (146.14 g/mol), or fumaric acid (116.07 g/mol)

The process temperature of 55° C. is imposed by the physicochemical constraints of the components; in example, dimethyl polyethylene glycol with a mean molecular weight 6000 D (PEG6000-di-Me, di-methyl ether) and sodium bicarbonate. The effervescent powder is comprising 100 g of a stoichiometric effervescent system formed of anhydrous succinic acid (43.2%)/sodium bicarbonate (56.8%) as moderately coarse powder or very fine powder, and a melt material is added finely powdered PEG6000-di-Me. After mixing in a Turbula mixer (T2A, Basel, Switzerland) at 28 rpm for 10 min, the effervescent mixture is transferred to a vertical fluidized bed dryer (Uni-Glatt, Binzen, Germany), adjusted first to 55° C. 61° C. and 123 m3/hr. Granulated material is obtained by the fusion of particles by melting PEG6000-di-Me for 5 min, 15 min, or 30 min. After cooling at 30% 63% relative humidity (RH) at ambient temperature for 30 min, the granules were screened with an oscillating granulator (Erweka F G S, Frankfurt, Germany) fixed at a moderate speed (II) and fitted with a 800-μm screen.

Measurement of Physical Properties of the Granulated Effervescent Material

Granule Flowability and Densides Granuleflowability and density were measured using 100 g of sample accurately weighed. The granule flowability was measured with a flow meter that consisted of a standardized funnel and a chronometer. Tapped densities were determined using a volume meter (Jel/Stav 2003A, Ludwigshafen, Germany).

Granule Size Distribution The granule size distribution was analyzed employing 100 g of granule and a vibrating Siever Retsch (Haan, Germany)(amplitude 1.5; 10 min) fitted with a European Pharmacopeial (3rd ed.) series of sieves (710, 500, 355, 250, 180, 125 μm). Mean granule size was determined graphically with a log-normal chart.

Effervescence Time The effervescence time was determined with 3 g of granules accurately weighed in a beaker containing 200 ml of distilled water at 20° C. The effervescence time was measured with a chronometer; the end of effervescence was reached when the solution became limpid and was without any particles.

Tableting The granule property of forming tablets with a resistance to crushing between 70N and 120N when compressed in a single-punch press was studied. After mixing in a Turbula mixer at 28 rpm for 10 min, 700 g of effervescent granules with sodium benzoate or siliconed sodium benzoate, we obtained granule mixtures ready to be compressed into tablets. Siliconed sodium benzoate was manufactured by mixing 600 g of very fine powder of sodium benzoate with 40 g of Silbione (silicone) for 30 min in a Kenwood planetary mixer at low speed (II). The mixture was screened with a 125-μm sieve. Silbione is an oil lubricant that could act to enhance the efficiency of sodium benzoate. Tablets were manufactured with a single-punch press (Frogerais O A, Evry Lisses, France) equipped with chromed punches 24 mm in diameter in a workroom in which air conditioning was adjusted to 30% 63% RH and 22° C. 61° C. Tablet weight, resistance to crushing (Erweka T B H 28, Heusenstamm, Germany), friability (Pharma Test PTF 1E, Haiberg, Germany), and effervescence time were evaluated using European Pharmacopeial methods (10th ed.). Tablet water content, carbon dioxide content, pH solution, tablets, and solution aspects were evaluated with the same methods for the granule. Sticking to the punch faces and die wall, capping, and sliding friction at the die wall were also evaluated visually. All formulas were compressed in constant conditions (depth of lower punch within the die was 6.98 mm, and the distance at which the upper punch penetrated the die was 6.04 mm) to select those tablets with weight above 2 g and resistance to crushing from 70 to 120N without processing problems during compression. Physicochemical The pH was determined with an Aquadata APH 1000 pH meter. Carbon Dioxide Content The carbon dioxide content from 3 g of granules accurately weighed or one tablet in 100 ml of diluted sulfuric acid (R) was determined with a sensitive balance, Mettler P G 503 S (Viroflay, France)(18, 19). The results were expressed as a loss of weight of the sample at the end of effervescence (mg $CO_2$ per gram of ES).

Using this procedure, the tablets typically will have a water content ≤0.1, a mean granule size of 510μ, a $CO_2$ content of 300 mg $CO_2$/g of granules, effervescent time 70 s minutes, a pH in the resulting solution of 5.6 and a typical dissolution volume in water or an ambient pharmaceutically acceptable carrier of 5 mL per tablet.

Example 5 In Vitro Anti-Biofilm Effect of Example Three Different Test Solutions of HOCl and Succinic Acid Three different test solutions were generated form the effervescent tablet. All three test solutions are generated from the effervescent tablet.

Experimental Setup

Test organisms: *Pseudomonas aeruginosa* or *Staphylococcus aureus* wild-type strains Biofilm type: 48 hours- or 24 hours-old biofilms grown on semipermeable membranes placed on solidified medium supplemented with 0.5% glucose. In the case of 48 h-old biofilms, the membranes with biofilms were transferred onto fresh plates after 24 h.

Initial viable cell amount: $5 \times 10^9$ colony forming units (CFUs)

Treatment method: Membranes with biofilms were transferred to new plates. Eight-10 layers of sterile gauze were placed on the second membrane, and 1 ml of antimicrobial solution was pipetted on the gauze layers. The treatment was carried out at room temperature for 2-to-3 h, or 4-to-6 h. In the case of the 4-to-6 h treatments, the gauze layers were replaced with fresh gauze layers with 1 ml sample solution 2 or 3 h after the treatments had been initiated.

Evaluation method: The gauze layers were discarded, and each membrane with biofilms was transferred into a 15 ml tube containing 5 ml 0.9% NaCl, vortexed for 10 sec., sonicated in an ultrasound bath for 10 min, and vortexed again for 10 sec. Ten-fold serial dilutions were made, and 10 ul of each dilution was spot-plated on LB plates for viable CFU counting.

Results and Conclusions

FIG. 2 shows the results obtained using the sample solutions. Increasing the acid activator concentrations from 0.25% to 1% and 2% in a 200 ppm HOCl solution gradually increased the killing of *S. aureus* biofilms. The effect of 1% glutaric acid alone had only minor effect on the biofilm. The three test solutions were compared to 4 different competing wound healing products on the market which all showed only minor effects on the *S. aureus* biofilms. An even stronger effect was shown for biofilms from *P. aeruginosa* It is concluded that hypochlorous acid and succinic acid at pH 4-7 acts synergistically and efficiently at concentrations that have shown to be safe in other studies.

Example 6 In Vivo Toxicity Studies

Example 6.1: 7-Day Inhalation Toxicity Study in Rats

A 7-day inhalation toxicity study in rats is performed as described by Kogel et al. in Food Chem Toxicol. 2014 June; 68:204-17. The rat inhalation study is performed according to the Organization for Economic Cooperation and Development (OECD). The test solution is generated from the effervescent tablet. Test Guideline 412, Sprague-Dawley rats is exposed to filtered fresh air (sham) as a reference, or the test solution. Care and use of the animals is in accordance with the American Association for Laboratory Animal Science Policy (1996). All animal experiments are approved by the Institutional Animal Care and Use Committee (IACUC). The histopathological evaluation is performed at defined anatomical sites of the nose and of the left lung according to a defined grading system. Free lung cells are determined in bronchoalveolar lavage fluid by flow cytometry, and inflammatory mediators are measured by multi-analytes profiling (MAP). For the Systems Toxicology approach, RNA samples from specific sites in the respiratory tract are obtained, i.e., respiratory nasal epithelium (RNE) and lung. For lung RNA isolation, respiratory epithelium of main bronchus and lung parenchyma is separated by Laser Capture Microdissection (LCM) and further processed, and analyzed on whole genome Affymetrix microarrays (GeneChip® Rat Genome 230 2.0 Array). No major perturbations are found related to inflammation, cell stress, cell proliferation in bronchi or lung parenchyma.

Example 7. Treatment of Mastitis

For applications where a color indicator in step 4 can add information in the therapeutic procedure, e.g. in or for indication of the oxidative activity of the API, the compartment comprising the ROD is included in the procedure.

Example 8. Clinical Antiviral Therapy

The medicine cup of Gima Aerosol Corsia Nebulizer is loaded with 5 mL of the test solution generated from the effervescent tablet. The mouth of a patient with a corona virus lung infection is attached to the hose and the face mask attached to the nebulizer, which is started After 10-15 minutes of breathing, the fluid is used up, and the nebulizer is turned off. The patient is monitored for several hours to secure that no side effects of the treatment is taking place. The mucosa and cilia of the patient is investigated for potential side effects.

INCORPORATION BY REFERENCE

Any and all references and citations to other documents, such as patents, patent applications, patent publications, journals, books, papers, web contents, that have been made throughout this disclosure are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

The invention claimed is:

1. An antimicrobial composition comprising:

a solid oxidized chlorine species salt according to the formula:

$$M^{n+}[Cl(O)_x]_n{}^{n-}$$

wherein M is an alkali metal, alkaline earth metal or transition metal ion, n is 1 or 2, and x is an integer from 1 to 4;

an acid activator with the formula:

$$RN(COOH)_m$$

or its salts, where RN is an organic moiety comprising 1-25 carbon atoms, saturated or unsaturated, optionally substituted with oxygen or hydrogen to form functional groups that cannot be oxidized by the chlorinated species, and m is an integer from 0 to 10;

a base activator that is able to react with the acid activator to generate carbon dioxide, having the formula:

$$(M^{n+})_s((H)_tCO_3)_u$$

wherein n is 1 or 2, s is 1 or 2, t is 0 or 1, u is 1 or 2, t+s+n is an integer from 1 to 5, and M is an alkali metal, an earth alkali metal, or a transition metal; and wherein the composition, when dissolved, has a pH between about 4 and 8.

2. The composition of claim 1, wherein said oxidized chlorine salt comprises an alkali metal or alkaline earth metal salt of hypochlorous acid.

3. The composition of claim 1, wherein said oxidized chlorine salt comprises an alkali metal or alkaline earth metal salt of chlorous acid.

4. The composition of claim 1, wherein said acid activator is selected from the group comprising monoacid, diacid, triacid, propionic acid, lactic acid, succinic, glutaric acid, pyruvic acid, citric acid, malic acid, oxaloacetic acid, tartaric acid, adipic acid, fumaric acid, heptanedioic acid, octanedioic acid, dioic acid, and derivatives thereof.

5. The composition of claim 1, wherein the base activator is selected from the group comprising sodium bicarbonate, potassium bicarbonate, sodium carbonate, and potassium carbonate.

6. The composition of claim 1, further comprising a water soluble polyol binder.

7. The composition of claim 1, further comprising a water soluble polyol binder selected from the group comprising monosaccharides, di-saccharides, polysaccharides or mono- or poly-hydroxy acids.

8. The composition of claim 1, further comprising a lubricant.

9. The composition of claim 1, further comprising a lubricant selected from the group comprising dextrose, lactose, sorbitol, ascorbic acid, sorbitol, mannitol, sodium benzoate, potassium sorbate, polyethylene glycol or derivatives thereof, succinic acid, adipic acid, glutaric acid or clavulanic acid.

10. The composition of claim 1, wherein the composition has an osmolality in the range of about 0.1 mOsm to about 500 mOsm.

11. The composition of claim 1, further comprising a viscosity-enhancing agent.

12. The composition of claim 11, wherein the viscosity-enhancing agent comprises a water-soluble gelling agent.

13. The composition of claim 12, wherein the water-soluble gelling agent is selected from the group consisting of poly acrylic acid, polyethylene glycol, poly(acrylic acid)-acrylamidoalkylpropane sulfonic acid co-polymer, phosphino polycarboxylic acid, poly(acrylic acid)-acrylamidoalkylpropane and sulfonic acid-sulfonated styrene terpolymers.

14. The composition of claim 1, further comprising a colour dye that provides visual indication of the presence of an oxidized chlorine compound.

15. The composition of claim 14, wherein the dye comprises a reduction-oxidation dye.

16. The composition of claim 14, wherein colour and intensity of colour of the dye is dependent on an oxidation state of the oxidized chlorine compound.

17. The composition of claim 1, wherein solid components are contained within an effervescent powder, granules, or tablet.

\* \* \* \* \*